United States Patent [19]
Hada et al.

[11] Patent Number: 5,929,271
[45] Date of Patent: Jul. 27, 1999

[54] COMPOUNDS FOR USE IN A POSITIVE-WORKING RESIST COMPOSITION

[75] Inventors: Hideo Hada, Hiratsuka; Kazufumi Sato, Sagamihara; Hiroshi Komano, Kanagawa-ken; Toshimasa Nakayama, Chigasaki, all of Japan

[73] Assignee: Tokyo Ohka Kogyo Co., Ltd., Japan

[21] Appl. No.: 08/912,123

[22] Filed: Aug. 15, 1997

[30] Foreign Application Priority Data

Aug. 20, 1996 [JP] Japan ...................................... 8-218803

[51] Int. Cl.$^6$ ...................................................... C07C 69/74
[52] U.S. Cl. .............................................................. 560/126
[58] Field of Search ............................................. 560/126

[56] References Cited

FOREIGN PATENT DOCUMENTS 4-39665  2/1992  Japan .
8-82925  3/1996  Japan .

*Primary Examiner*—Samuel Barts
*Assistant Examiner*—Rosalynd Keys
*Attorney, Agent, or Firm*—Wenderoth, Lind & Ponack, L.L.P.

[57] ABSTRACT

Proposed is novel compounds for use in a chemical-sensitization positive-working photoresist composition used in the photolithographic patterning process for the manufacture of fine electronic devices, which is capable of giving, with high photosensitivity to ArF excimer laser beams, a patterned resist layer having an excellently orthogonal cross sectional profile and high resistance against dry etching and exhibiting good adhesion to the substrate surface. While the composition comprises (A) a film-forming resinous ingredient which causes an increase of alkali solubility by interacting with an acid and (B) a radiation-sensitive acid-generating agent, the most characteristic feature of the invention consists in the use of a specific acrylic resin as the component (A), which comprises the monomeric units of a (meth)acrylic acid ester of hydroxy bicyclo[3.1.1]heptanone unsubstituted or substituted by an alkyl group such as hydroxypinanone (meth)acrylate, optionally, in combination with the monomeric units derived from (meth)acrylic acid and/or tert-butyl (meth)acrylate in a molar fraction of 3:7 to 7:3.

2 Claims, No Drawings

COMPOUNDS FOR USE IN A POSITIVE-WORKING RESIST COMPOSITION

BACKGROUND OF THE INVENTION

The present invention relates to a novel positive-working resist composition or, more particularly, to a novel chemical-sensitization positive-working photoresist composition with high sensitivity having high transparency to the ArF excimer laser beams and capable of giving a positively patterned resist layer having excellently orthogonal cross sectional profile and high resistance against dry etching as well as high adhesion to the substrate surface.

It is a remarkable trend in recent years that the photolithographic patterning works in the manufacture of various kinds of electronic devices such as semiconductor devices and liquid crystal display panels are conducted increasingly by using a chemical-sensitization photoresist composition in place of conventional photoresist composition of other types. A chemical-sensitization photoresist composition contains a radiation-sensitive acid-generating compound from which an acid is released in the photoresist layer by the pattern-wise exposure to actinic rays while the thus generated acid catalytically acts on the film-forming resinous ingredient of the composition which causes, by the interaction with an acid, a change of the solubility in an aqueous alkaline developer solution. Accordingly, chemical-sensitization photoresist compositions are advantageous in respects of their high photosensitivity and high pattern resolution even with a relatively low content of the acid-generating agent.

Chemical-sensitization photoresist compositions are classified into positive-working and negative-working compositions depending on the types of the film-forming resinous ingredients which cause an increase and decrease, respectively, of the solubility in an aqueous alkaline developer solution by interacting with the acid generated from the acid-generating agent when the resist layer is pattern-wise exposed to actinic rays.

The most important resinous compound suitable as the above mentioned film-forming resinous ingredient in the chemical-sensitization photoresist compositions is a polyhydroxystyrene resin optionally substituted for a part of the hydroxyl groups therein by acid-dissociable solubility-reducing groups in view of the high transparency of the resin to the KrF excimer laser beams of 248 nm wavelength used as the actinic rays for pattern-wise exposure.

Along with the trend in the modern semiconductor devices toward finer and finer patterning of the resist layer, the photolithographic process by using ArF excimer laser beams of 193 nm wavelength is now on the starting line to replace the process by using KrF excimer laser beams of 248 nm wavelength. Since resinous ingredients having a benzene ring in the molecular structure, such as the above mentioned polyhydroxystyrene, can hardly be used in the photolithographic patterning process by using the ArF excimer laser beams due to the relatively low transparency of the resin to the light of such a short wavelength, proposals have been made for resins usable in the ArF excimer laser beam process, of which acrylic resins such as polymethyl methacrylate are now highlighted.

As such an acrylic resin capable of satisfying both of the requirements for the UV transparency and dry etching resistance, proposals are made for polymers of an acrylic acid ester having an alicyclic hydrocarbon group introduced into the ester-forming part including, for example, polymeric resins of a (meth)acrylic acid ester having an adamantane structure in the ester-forming group disclosed in Japanese Patent Kokai 4-39665 and polymeric resins of a (meth)acrylic acid ester having a terpenoid ring structure, such as menthol residue, in the ester-forming group disclosed in Japanese Patent Kokai 8-82925.

The above mentioned resins of a (meth)acrylic acid ester having an adamantane structure, however, are not practicable because, in addition to the expensiveness, the photosensitivity of the photoresist compositions formulated with such a resin is not high enough and the resist composition cannot give a patterned resist layer having an excellently orthogonal cross sectional profile and the photoresist compositions formulated with a resin of a (meth)acrylic acid ester having a terpenoid, e.g., menthol, structure cannot give a resist layer having high resistance against dry etching.

While the process using the ArF excimer laser beams has been developed with an object to accomplish good pattern resolution for ultrafine patterning with a line width of 0.2 $\mu$m or even smaller, an important requirement in such ultrafine patterning is high adhesion between the substrate surface and the patterned resist layer formed thereon since otherwise troubles are sometimes caused due to failure of patterning.

SUMMARY OF THE INVENTION

The present invention accordingly has an object, in view of the above described problems in the prior art, to provide a novel chemical-sensitization positive-working photoresist composition having high transparency to the ArF excimer laser beams to exhibit high photosensitivity and capable of giving a positively patterned resist layer excellent in the cross sectional profile, resistance against dry etching and adhesion to the substrate surface.

Thus, the chemical-sensitization positive-working photoresist composition provided by the present invention comprises, as a uniform solution in an organic solvent:

(A) 100 parts by weight of a film-forming acrylic resin which causes an increase of the solubility in an aqueous alkaline solution by interacting with an acid; and (B) from 0.5 to 20 parts by weight of a radiation-sensitive acid-generating agent which is a compound capable of releasing an acid when irradiated with actinic rays, the acrylic resin as the component (A) being a polymer or copolymer comprising the monomeric units of a (meth) acrylic acid ester of hydroxy bicyclo[3.1.1]heptanone unsubstituted or substituted on the bicycloheptanone structure by a lower alkyl group, such as hydroxy bicyclo[3.1.1] pinanone. Incidentally, acrylate and methacrylate of 2-hydroxy-3-pinanone are each a novel compound not known in the prior art or not described in literatures.

When the acrylic resin as the component (A) is a copolymer consisting of the monomeric units of the (meth)acrylic acid ester of hydroxy bicyclo[3.1.1]heptanone and monomeric units of a comonomer, the comonomer is selected from the group consisting of acrylic acid, methacrylic acid and tert-butyl esters thereof and the molar fraction of the former monomeric units is at least 30% or, preferably, in the range from 30% to 70%.

DETAILED DESCRIPTION OF THE PREFERRED EMBODIMENTS

The component (A) in the inventive photoresist composition, which is required to cause an increase of the solubility in an aqueous alkaline solution by the interaction with an acid, is an acrylic resin insolubilized in an alkaline solution by substitution for at least a part of the carboxylic groups by acid-dissociable solubility-reducing groups which are dissociated in the presence of an acid to increase the alkali solubility of the resin.

The acrylic resin as the component (A) of the inventive composition is a polymer or copolymer comprising the monomeric units of a (meth)acrylic acid ester of hydroxy bicyclo[3.1.1]heptanone unsubstituted or substituted by a lower alkyl group. This specific acrylic resin is advantageous as the film-forming resinous ingredient of a chemical-sensitization positive-working photoresist composition to be used in the ArF excimer laser process of patterning because, besides the inexpensiveness of the resin, the resin is highly transparent to the ArF excimer laser beams to ensure high photosensitivity of the composition and capable of giving a patterned resist layer having an excellently orthogonal cross sectional profile, high resistance against dry etching and good adhesion to the substrate surface.

It is essential in the photoresist composition of the invention that the acrylic resin as the component (A) comprises the monomeric units represented by the general formula (I)

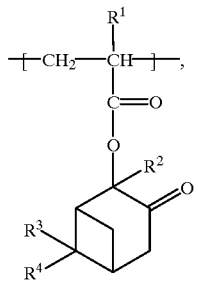

in which $R^1$ is a hydrogen atom or a methyl group and $R^2$, $R^3$ and $R^4$ are each, independently from the others, a hydrogen atom or a lower alkyl group having 1 to 4 carbon atoms including methyl, ethyl, propyl and butyl groups which may be straightly linear or branched. In particular, $R^2$ is preferably an alkyl group since the acid-dissociability of the ester-forming group is low when $R^2$ is a hydrogen atom. More preferably, $R^2$, $R^3$ and $R^4$ are each a methyl group. The unexpectedly good adhesion between the substrate surface and the resist layer formed from the inventive resist composition is presumably due to the structure of the ester-forming group in which one of the carbon atoms adjacent the carbon atom of the alicyclic hydroxyl group, i.e. the carbon atom bonded to the group $R^2$, is a carbonyl carbon.

The above defined monomeric units represented by the general formula (I) can be introduced into the acrylic resin as the component (A) by conducting homopolymerization or copolymerization involving an acrylic monomer represented by the general formula (II)

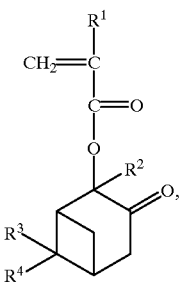

in which each of the symbols has the same meaning as defined for the general formula (I).

Although the acrylic resin as the component (A) in the inventive photoresist composition can be a homopolymer consisting of a single kind of the monomeric units expressed by the general formula (I) alone, it is preferable that the acrylic resin is a copolymer of which the molar fraction of the monomeric units expressed by the general formula (I) is in the range from 30% to 70%, the balance of the monomeric units being derived from a comonomer or comonomers other than the monomer of the formula (II), in order to obtain a high-level balance of various properties such as transparency of the resist layer to actinic rays, high dry etching resistance of the resist layer and good adhesion between the resist layer and the substrate surface.

The above mentioned comonomer to be copolymerized with the (meth)acrylic monomer of the formula (II) to form the copolymer as the acrylic resin of the component (A) can be selected from the classes (1), (2) and (3) of monomeric compounds specified below.

(1) The comonomer of this class includes acrylic or methacrylic acid substituted for the carboxylic group by a group which serves to increase the dry etching resistance of the resist layer or an acid-dissociable group which serves to decrease the alkali solubility of the resin. They are known in the formulation of chemical-sensitization positive-working photoresist compositions as exemplified by: tert-butyl (meth)acrylate, 3-oxocyclohexyl (meth)acrylate, adamantyl (meth)acrylate, cyclohexyl (meth)acrylate and tricyclodecanyl (meth)acrylate. Preferably, the comonomer is selected from the group consisting of tert-butyl, cyclohexyl, 2-naphthyl, benzyl, 2-tetrahydropyranyl, 3-cyclohexanonyl, 2-bicyclo-[2.2.1]heptyl, 1-tricyclo[3.3.1.1$^{3.7}$]decanyl and 9-tricyclo-[5.2.1.0$^{2.6}$]decanyl (meth)acrylates.

(2) The acrylic resin is imparted with increased alkali solubility when the comonomer is an ethylenically unsaturated carboxylic acid such as acrylic acid, methacrylic acid, maleic acid and fumaric acid.

(3) Included in this class are known monomers conventionally used in acrylic resins as exemplified by alkyl (meth)acrylates such as methyl, ethyl, propyl, isopropyl, butyl, isobutyl, n-hexyl, n-octyl, 2-ethylhexyl, lauryl, 2-hydroxyethyl and 2-hydroxypropyl (meth)acrylates, unsaturated amides such as (meth)acrylamide, N-methylol (meth)acrylamide and diacetone acrylamide and vinyl monomers such as (meth)acrylonitrile, vinyl chloride and ethyl vinyl ether.

While the acrylic resin as the component (A) can be a copolymer of the monomeric compound of the general formula (II) and any one or any combination of the comonomers belonging to the above described classes (1), (2) and (3), the comonomeric constituent for the copolymerization is preferably a combination of a comonomer belonging to the monomers of class (1) and a comonomer belonging to the monomers of class (2) or, in particular, a combination of tert-butyl (meth)acrylate and (meth)acrylic acid.

When the acrylic resin as the component (A) is a copolymer consisting of the monomeric units of the general formula (I) and comonomeric units derived from the comonomers of the classes (1) to (3), the molar fraction of the monomeric units of the formula (I) is preferably in the range from 30% to 70% or, more preferably, from 50% to 65% in consideration of the properties of the photoresist composition to give a patterned resist layer having high dry etching resistance, good adhesion to the substrate surface and high contrast between the exposed and unexposed areas. The molar fraction of the monomeric units derived from the comonomers (1) and/or (3) is selected in the range from 10% to 60% or, preferably, from 15% to 30% and the molar fraction of the monomeric units derived from the comonomers (2) is selected in the range not exceeding 30% or, preferably, from 10% to 20%.

The radiation-sensitive acid-generating agent as the component (B) in the inventive photoresist composition is not particularly limitative and can be freely selected from those acid-generating compounds used as the acid-generating agent in conventional chemical-sensitization photoresist compositions.

Examples of suitable acid-generating compounds include those compounds belonging to the classes (1) to (7) specified below.
(1) Bissulfonyl diazomethane compounds such as bis(p-toluenesulfonyl) diazomethane, bis(1,1-dimethylethylsulfonyl) diazomethane, bis (cyclohexylsulfonyl) diazomethane and bis(2,4-dimethylphenylsulfonyl) diazomethane
(2) Nitrobenzyl compounds such as 2-nitrobenzyl p-toluenesulfonate and 2,6-dinitrobenzyl p-toluenesulfonate
(3) Sulfonic acid ester compounds such as pyrogallol trimesylate and pyrogallol tritosylate
(4) Onium salt compounds such as diphenyliodonium hexafluorophosphate, (4-methoxyphenyl) phenyliodonium trifluoromethane sulfonate, bis(p-tert-butylphenyl)iodonium trifluoromethane sulfonate, triphenylphosphonium hexafluorophosphate, (4-methoxyphenyl)diphenylsulfonium trifluoromethane sulfonate and (p-tert-butylphenyl)diphenylsulfonium trifluoromethane sulfonate
(5) Benzoin tosylate compounds such as benzoin tosylate and α-methylbenzoin tosylate
(6) Halogen-containing triazine compounds such as:
2-(4-methoxyphenyl)-4,6-bis(trichloromethyl)-1,3,5-triazine,
2-(4-methoxynaphthyl)-4,6-bis(trichloromethyl)-1,3,5-triazine,
2-[2-(2-furyl)ethenyl-4,6-bis(trichloromethyl)-1,3,5-triazine,
2-[2-(5-methyl-2-furyl)ethenyl-4,6-bis(trichloromethyl)-1,3,5-triazine,
2-[2-(3,5-dimethoxyphenyl)ethenyl-4,6-bis(trichloromethyl)-1,3,5-triazine,
2-[2-(3,4-dimethoxyphenyl)ethenyl-4,6-bis(trichloromethyl)-1,3,5-triazine,
2-(3,4-methylenedioxyphenyl)-4,6-bis(trichloromethyl)-1,3,5-triazine,
2,4,6-tris(2,3-dibromopropyl)-1,3,5-triazine and tris(2,3-dibromopropyl) isocyanurate
(7) Cyano group-containing oximesulfonate compounds such as those disclosed in Japanese Patent Kokai 60-65072 including:

α-(p-toluenesulfonyloxyimino)benzyl cyanide,
α-(p-chlorobenzenesulfonyloxyimino)benzyl cyanide,
α-(4-nitrobenzenesulfonyloxyimino)benzyl cyanide,
α-(4-nitro-2-trifluoromethylbenzenesulfonyloxyimino) benzyl cyanide,
α-(benzenesulfonyloxyimino)-4-chlorobenzyl cyanide,
α-(benzenesulfonyloxyimino)-2,4-dichlorobenzyl cyanide,
α-(benzenesulfonyloxyimino)-2,6-dichlorobenzyl cyanide,
α-(benzenesulfonyloxyimino)-4-methoxybenzyl cyanide,
α-(2-chlorobenzenesulfonyloxyimino)-4-methoxybenzyl cyanide,
α-(benzenesulfonyloxyimino)thien-2-yl acetonitrile,
α-[4-dodecylbenzenesulfonyloxyimino)benzyl cyanide,
α-[(toluenesulfonyloxyimino)-4-methoxyphenyl] acetonitrile,
α-[(dodecylbenzenesulfonyloxyimino)-4-methoxyphenyl] acetonitrile, and
α-(tosyloxyimino)-4-thienyl cyanide, as well as those compounds represented by the general formulas $$R^6-C(CN)=N-O-SO_2-R^7, \qquad (III)$$

in which $R^6$ and $R^7$ are each a non-aromatic group, $$R^8-C(CN)=N-O-SO_2-R^9, \qquad (IV)$$

in which $R^8$ is an aromatic group and $R^9$ is a lower alkyl group or a halogenated lower alkyl group, and $$A[-C(CN)=N-O-SO_2-R^{10}]_n, \qquad (V)$$

in which the subscript n is 2 or 3, A is a divalent, when n is 2, or tervalent, when n is 3, organic group and $R^{10}$ is a substituted or unsubstituted monovalent hydrocarbon group The non-aromatic group denoted by $R^6$ or $R^7$ in the general formula (III) is exemplified by alkyl, halogenoalkyl, alkenyl, cycloalkyl, cycloalkenyl, alkoxy, cycloalkoxy and adamantyl groups. The alkyl group, which may be straightly linear or branched, has 1 to 12 carbon atoms and includes methyl, ethyl, n-propyl, isopropyl, n-butyl, isobutyl, sec-butyl, tert-butyl, n-pentyl, n-octyl and n-dodecyl groups. In the halogenoalkyl groups, which preferably has 1 to 4 carbon atoms, the halogen is not particularly limitative including fluorine, chlorine, bromine and iodine and the number of the halogen atoms in a halogenoalkyl group is not limited to one. Examples of the halogenoalkyl group include chloromethyl, trichloromethyl, trifluoromethyl and 3-bromopropyl groups.

The alkenyl group denoted by $R^6$ or $R^7$ in the general formula (III), which preferably has 2 to 6 carbon atoms, can be straightly linear or branched and is exemplified by vinyl, 1-propenyl, isopropenyl and 2-butenyl groups. The cycloalkyl group, which preferably has 5 to 12 carbon atoms, is exemplified by cyclopentyl, cyclohexyl, cyclooctyl and cyclododecyl groups. The cycloalkenyl group, which preferably has 4 to 8 carbon atoms, is exemplified by 1-cyclobutenyl, 1-cyclopentenyl, 1-cyclohexenyl, 1-cycloheptenyl and 1-cyclooctenyl groups. The alkoxy group, which preferably has 1 to 8 carbon atoms, is exemplified by methoxy, ethoxy, propoxy, butoxy and pentoxy groups. The cycloalkoxy group, which preferably has 5 to 8 carbon atoms, is exemplified by cyclopentoxy and cyclohexyloxy groups. In particular, the group denoted by $R^6$ is selected from alkyl, cycloalkyl and cycloalkenyl groups or, preferably, from cycloalkenyl groups and the group denoted by $R^7$ is selected from alkyl, halogenoalkyl and cycloalkyl groups or, preferably, from alkyl groups. Most preferably, the compound has a cyclopentenyl group as $R^6$ and an alkyl group of 1 to 4 carbon atoms as $R^7$.

Particular examples of the oximesulfonate compound expressed by the general formula (III) include:
α-(methylsulfonyloxyimino)-1-cyclopentenyl acetonitrile,
α-(methylsulfonyloxyimino)-1-cyclohexenyl acetonitrile,
α-(methylsulfonyloxyimino)-1-cycloheptenyl acetonitrile,
α-(methylsulfonyloxyimino)-1-cyclooctenyl acetonitrile,
α-(trifluoromethylsulfonyloxyimino)-1-cyclopentenyl acetonitrile,
α-(trifluoromethylsulfonyloxyimino)cyclohexyl acetonitrile,
α-(ethylsulfonyloxyimino)ethyl acetonitrile,
α-(propylsulfonyloxyimino)propyl acetonitrile,
α-(cyclohexylsulfonyloxyimino)cyclopentyl acetonitrile,
α-(cyclohexylsulfonyloxyimino)cyclohexyl acetonitrile,
α-(cyclohexylsulfonyloxyimino)-1-cyclopentenyl acetonitrile,
α-(ethylsulfonyloxyimino)-1-cyclopentenyl acetonitrile,
α-(isopropylsulfonyloxyimino)-1-cyclopentenyl acetonitrile,
α-(n-butylsulfonyloxyimino)-1-cyclopentenyl acetonitrile,
α-(ethylsulfonyloxyimino)-1-cyclohexenyl acetonitrile,
α-(isopropylsulfonyloxyimino)-1-cyclohexenyl acetonitrile, and
α-(n-butylsulfonyloxyimino)-1-cyclohexenyl acetonitrile.

The aromatic group denoted by $R^8$ in the above given general formula (IV) is exemplified by phenyl, naphthyl, furyl and thienyl groups which can optionally be substituted by one or more of halogen atoms, alkyl groups, alkoxy groups, nitro groups and the like. The lower alkyl groups as a class of the groups denoted by $R^9$ are exemplified by the straightly linear or branched alkyl groups having 1 to 4 carbon atoms such as methyl, ethyl, n-propyl, isopropyl, n-butyl, isobutyl, sec-butyl and tert-butyl groups. The halogenoalkyl groups as the other class of the groups denoted by $R^9$ are exemplified by the halogenoalkyl groups having 1 to 4 carbon atoms such as chloromethyl, trichloromethyl, trifluoromethyl and 2-bromopropyl groups.

Particular examples of the oximesulfonate compound expressed by the general formula (IV) include:
α-(methylsulfonyloxyimino)phenyl acetonitrile,
α-(methylsulfonyloxyimino)-4-methoxyphenyl acetonitrile,
α-(trifluoromethylsulfonyloxyimino)phenyl acetonitrile,
α-(trifluoromethylsulfonyloxyimino)-4-methoxyphenyl acetonitrile,
α-(ethylsulfonyloxyimino)-4-methoxyphenyl acetonitrile,
α-(propylsulfonyloxyimino)-4-methylphenyl acetonitrile and
α-(methylsulfonyloxyimino)-4-bromophenyl acetonitrile.

The hydrocarbon groups as a class of the groups denoted by $R^{10}$ in the general formula (V) include aromatic and non-aromatic hydrocarbon groups. The aromatic group should preferably have 6 to 14 carbon atoms as exemplified by phenyl, tolyl, methoxyphenyl, xylyl, biphenyl, naphthyl and anthryl groups as well as heterocyclic groups such as furanyl, pyridyl and quinolyl groups. The non-aromatic hydrocarbon group, which is free from an aromatic ring structure such as benzene, naphthalene, furan, thiophene and pyridine rings, includes aliphatic hydrocarbon groups and alicyclic hydrocarbon groups such as alkyl, alkenyl, cycloalkyl and cycloalkenyl groups. The alkyl groups, which may be straightly linear or branched, preferably have 1 to 12 carbon atoms as exemplified by methyl, ethyl, propyl, isopropyl, n-butyl, sec-butyl, tert-butyl, n-pentyl, n-octyl and n-dodecyl groups. The alkenyl groups preferably have 2 to 12 carbon atoms as exemplified by ethenyl, propenyl, butenyl, butadienyl, hexenyl and octadienyl groups. The cycloalkyl groups, which preferably have 4 to 12 carbon atoms, are exemplified by cyclopentyl, cyclohexyl, cyclooctyl and cyclododecyl groups. The cycloalkenyl groups, which preferably have 4 to 12 carbon atoms, are exemplified by 1-cyclobutenyl, 1-cyclopentenyl, 1-cyclohexenyl, 1-cycloheptenyl and 1-cyclooctenyl groups.

The substituted hydrocarbon groups as the other class of the groups denoted by $R^{10}$ are exemplified by those obtained by the substitution of one or more substituent groups for the hydrogen atoms of the above named aromatic or non-aromatic hydrocarbon groups, of which those substituted by halogen atoms, e.g., chlorine, bromine and fluorine atoms, hydroxyl groups, alkoxy groups and acyl groups are preferable or, in particular, halogenated aryl groups and halogenated alkyl groups are more preferable. Suitable halogenated alkyl groups include those having 1 to 4 carbon atoms such as chloromethyl, trichloromethyl, trifluoromethyl and 2-bromopropyl groups.

The divalent or tervalent organic group denoted by A in the general formula (V) is preferably a divalent or tervalent, aliphatic or aromatic hydrocarbon group.

Examples of the oximesulfonate compounds expressed by the general formula (V), in which the group denoted by $R^{10}$ is a non-aromatic hydrocarbon group, include the compounds expressed by the following structural formulas, in which Me is a methyl group, Et is an ethyl group, Bu is a butyl group, fMe is a trifluoromethyl group, Ch is a cyclohexyl group, pPn is a 1,4-phenylene group and mPn is a 1,3-phenylene group:

Me—SO$_2$—O—N=C(CN)—pPn—C(CN)=N—O—SO$_2$—Me;
Me—SO$_2$—O—N=C(CN)—mPn—C(CN)=N—O—SO$_2$—Me;
Et—SO$_2$—O—N=C(CN)—pPn—C(CN)=N—O—SO$_2$—Et;
Bu—SO$_2$—O—N=C(CN)—mPn—C(CN)=N—O—SO$_2$—Bu;
Bu—SO$_2$—O—N=C(CN)—pPn—C(CN)=N—O—SO$_2$—Bu;
fMe—SO$_2$—O—N=C(CN)—pPn—C(CN)=N—O—SO$_2$—fMe;
fMe—SO$_2$—O—N=C(CN)—mPn—C(CN)=N—O—SO$_2$—fMe; and
Ch—SO$_2$—O—N=C(CN)—pPn—C(CN)=N—O—SO$_2$—Ch.

Further, examples of the oximesulfonate compounds expressed by the general formula (V), in which the group denoted by $R^{10}$ is an aromatic hydrocarbon group, include the compounds expressed by the following structural formulas, in which Me is a methyl group, Ph is a phenyl group, pPn is a 1,4-phenylene group and mPn is a 1,3-phenylene group:

Ph—SO$_2$—O—N=C(CN)—pPn—C(CN)=N—O—SO$_2$—Ph;
MeO—pPn—SO$_2$—O—N=C(CN)—pPn—C(CN)=N—O—SO$_2$—pPn—OMe;
Me—pPn—SO$_2$—O—N=C(CN)—mPn—C(CN)=N—O—SO$_2$—pPn—Me; and
MeO—pPn—SO$_2$—O—N=C(CN)—mPn—C(CN)=N—O—SO$_2$—pPn—OMe.

Among the above described various classes of acid-generating compounds, which can be used either singly or as a combination of two kinds or more according to need, the onium salt compounds and cyano group-containing oximesulfonate compounds are particularly preferable as the radiation-sensitive acid-generating agent in the inventive chemical-sensitization positive-working photoresist compositions.

In the formulation of the inventive chemical-sensitization positive-working photoresist composition, the amount of the above described acid-generating agent is in the range from 0.5 to 20 parts by weight or, preferably, from 1 to 10 parts by weight per 100 parts by weight of the component (A). When the amount of the component (B) is too small, pattern reproduction in the photoresist layer would be incomplete while, when the amount thereof is too large, a photoresist solution of good uniformity can hardly be obtained and the storage stability of the resist solution is somewhat decreased.

The chemical-sensitization positive-working photoresist composition of the invention is used in the form of a uniform solution prepared by dissolving the above described essential ingredients and optional ingredients in an organic solvent. Examples of suitable organic solvents include: ketone solvents such as acetone, methyl ethyl ketone, cyclohexanone, methyl isoamyl ketone and 2-heptanone; polyhydric alcohols and derivatives thereof such as ethyleneglycol, ethyleneglycol monoacetate, diethyleneglycol, diethyleneglycol monoacetate, propyleneglycol, propyleneglycol monoacetate, dipropyleneglycol and dipropyleneglycol monoacetate as well as monomethyl, monoethyl, monopropyl, monobutyl and monophenyl ethers thereof; cyclic ether solvents such as dioxane; and ester solvents such as methyl lactate, ethyl lactate, methyl acetate, ethyl acetate, butyl acetate, methyl pyruvate, ethyl pyruvate, methyl methoxypropionate and ethyl ethoxypropionate. These organic solvents can be used either singly or as a mixture of two kinds or more according to need.

It is of course optional according to need that the photoresist composition of the invention is admixed with various kinds of known additives formulated in conventional photoresist compositions including, for example, auxiliary resins to improve the properties of the resist film, plasticizers, stabilizers, coloring agents, surface active agents and others each in a limited amount.

The photolithographic patterning process by using the inventive photoresist composition is not particularly different from the processes by using conventional photoresist compositions. Namely, a substrate such as a semiconductor silicon wafer is coated with the photoresist solution by using a suitable coating machine such as spinners followed by drying to give a dried photoresist layer which is pattern-wise exposed, for example, to ArF excimer laser beams through a pattern-bearing photomask on an exposure machine to form a latent image of the pattern in the resist layer followed by a post-exposure baking treatment. Thereafter, the resist layer having the latent image of the pattern is subjected to a development treatment with an aqueous alkaline developer solution which is typically a 0.1 to 10% by weight aqueous solution of tetramethylammonium hydroxide so that the resist layer in the areas exposed to the actinic rays is dissolved away to leave a positively patterned resist layer having high fidelity to the photomask pattern.

In the following, the chemical-sensitization positive-working photoresist composition of the invention is described in detail by way of Examples as preceded by a description of the procedure for the preparation of the specific acrylic resins used as the component (A) in the formulation of the photoresist compositions.

PREPARATION EXAMPLE 1

2-Hydroxy-3-pinanone methacrylate, which is a novel compound not known in the prior art or not described in any literatures, was synthesized in the following manner. Thus, 50 g (0.3 mole) of 2-hydroxy-3-pinanone and 60 g (0.6 mole) of triethylamine were dissolved with thorough agitation in 200 ml of tetrahydrofuran to form a solution, into which 62.4 g (0.6 mole) of methacryloyl chloride were added dropwise at 25° C. over a period of 1 hour to give a reaction mixture.

The reaction mixture was agitated for 24 hours at 25° C. to effect the reaction followed by filtration thereof. The filtrate obtained by filtration of the reaction mixture was freed from the solvent by distillation to give a reaction product which was dissolved in 300 ml of diethyl ether and the solution was washed 10 times with a 10% by weight aqueous solution of sodium hydroxide. The reaction product in the ether solution was subjected to a column chromatographic purification using n-heptane as the eluant to give a colorless liquid product which could be identified to be the desired 2-hydroxy-3-pinanone methacrylate from the analytical results.

Namely, the $^1$H-NMR spectrum of the product compound (solvent: acetone-$d_6$) had peaks at δ values of 0.90 ppm, 1.40 ppm, 1.60 ppm, 1.85 to 2.95 ppm, 5.5 ppm and 5.97 ppm.

PREPARATION EXAMPLE 2

A copolymerization reaction of three comonomers including the 2-hydroxy-3-pinanone methacrylate prepared in Preparation Example 1 described above, tert-butyl methacrylate and methacrylic acid was conducted by heating a polymerization mixture, which was prepared by dissolving 100 g (0.46 mole) of the first comonomer, 20 g (0.14 mole) of the second comonomer and 12 g (0.14 mole) of the third comonomer in 560 g of tetrahydrofuran with addition of 4.5 g of azobisisobutyronitrile as a polymerization initiator, at 75° C. for 3 hours.

After termination of the polymerization reaction in the above described manner, the polymerization mixture was poured into 20 liters of n-heptane to precipitate the polymer which was freed from the solvent and dried at room temperature under reduced pressure to give 60 g of a copolymer of 2-hydroxy-3-pinanone methacrylate, tert-butyl methacrylate and methacrylic acid. This copolymer product had a weight-average molecular weight of 11000 and the dispersion of the molecular weight distribution was 1.6 as expressed by the ratio of the weight-average molecular weight to the number-average molecular weight.

PREPARATION EXAMPLE 3 (COMPARATIVE)

The procedure for the preparation of a copolymer was substantially the same as in Preparation Example 2 described above excepting for the replacement of the 2-hydroxy-3-pinanone methacrylate with the same amount of adamantyl methacrylate expressed by the structural formula

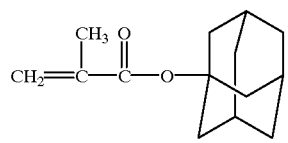

to give 45 g of a ternary copolymer of adamantyl methacrylate, tert-butyl methacrylate and methacrylic acid. This copolymer product had a weight-average molecular weight of 9500 and the dispersion of the molecular weight distribution was 1.5 as expressed by the ratio of the weight-average molecular weight to the number-average molecular weight.

PREPARATION EXAMPLE 4 (COMPARATIVE)

The procedure for the preparation of a copolymer was substantially the same as in Preparation Example 2 described above excepting for the replacement of 100 g of the 2-hydroxy-3-pinanone methacrylate with 87 g (0.40 mole) of tricyclodecanyl methacrylate expressed by the structural formula

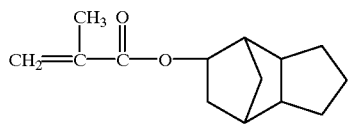

to give 75 g of a ternary copolymer of tricyclodecanyl methacrylate, tert-butyl methacrylate and methacrylic acid. This copolymer product had a weight-average molecular weight of 11500 and the dispersion of the molecular weight distribution was 1.6 as expressed by the ratio of the weight-average molecular weight to the number-average molecular weight.

PREPARATION EXAMPLE 5 (COMPARATIVE)

A copolymerization reaction of methyl methacrylate, tert-butyl methacrylate and methacrylic acid was conducted by heating a polymerization mixture, which was prepared by dissolving 30 g (0.34 mole) of the first comonomer, 15.7 g (0.11 mole) of the second comonomer and 7.57 g (0.09 mole) of the third comonomer in 400 g of tetrahydrofuran with addition of 3.2 g of azobisisobutyronitrile as a polymerization initiator, at 75° C. for 3 hours.

After completion of the polymerization reaction in the above described manner, the polymerization mixture was poured into 10 liters of n-heptane to precipitate the polymer which was freed from the solvent and dried at room temperature under reduced pressure to give 40 g of a copolymer of methyl methacrylate, tert-butyl methacrylate and methacrylic acid. This copolymer product had a weight-average molecular weight of 12500 and the dispersion of the molecular weight distribution was 1.7 as expressed by the ratio of the weight-average molecular weight to the number-average molecular weight.

EXAMPLE 1

A positive-working photoresist solution was prepared by dissolving 100 parts by weight of the copolymer obtained in Preparation Example 2 and 2 parts by weight of bis(tert-butylphenyl)iodonium trifluoromethanesulfonate in 680 parts by weight of propyleneglycol monomethyl ether acetate.

A semiconductor silicon wafer was coated with the thus prepared photoresist solution on a spinner followed by drying on a hot plate at 150° C. for 90 seconds to give a dried photoresist layer having a thickness of 0.5 μm. The photoresist layer was pattern-wise exposed to ArF excimer laser beams of 193 nm wavelength on an ArF exposure machine (manufactured by Nikon Co.) and then subjected to a post-exposure baking treatment at 110° C. for 90 seconds followed by a development treatment for 65 seconds in a 0.238% by weight aqueous solution of tetramethylammonium hydroxide, rinse in a running stream of water for 30 seconds and drying to complete a patterned resist layer.

The photosensitivity of the photoresist composition in the patterning process described above was estimated by recording the minimum exposure dose in mJ/cm² necessitated for the reproduction of a line-and-space pattern of 0.25 μm line and space widths to give a line-and-space patterned resist layer with a line width to space width ratio of 1:1 as a measure of the photosensitivity to find a value of 25 mJ/cm².

The above obtained line-and-space patterned resist layer of 0.25 μm line width had an orthogonal cross sectional profile standing upright on the substrate surface as examined on a scanning electron microscopic photograph. Further, pattern resolution thereof was complete without patterning failure in a line-and-space patterned resist layer having a line width of as small as 0.20 μm.

In the next place, the resist layer was subjected to a test of dry etching resistance by conducting a dry etching treatment on an etching instrument (Model OAPM-406, manufactured by Tokyo Ohka Kogyo Co.) using a gaseous mixture of oxygen and tetrafluoromethane as the etching gas to find that the rate of film thickness reduction per unit time was 90% based on the rate with a polyhydroxystyrene resin film.

EXAMPLE 2

Another positive-working photoresist solution was prepared by dissolving 100 parts by weight of the copolymer obtained in Preparation Example 2 and 3 parts by weight of α-(p-toluenesulfonyloxyimino)benzyl cyanide in 680 parts by weight of propyleneglycol monomethyl ether acetate.

A semiconductor silicon wafer was coated with the thus prepared photoresist solution on a spinner followed by drying on a hot plate at 100° C. for 90 seconds to give a dried photoresist layer having a thickness of 0.5 μm. The photoresist layer was pattern-wise exposed to ArF excimer laser beams of 193 nm wavelength on an ArF exposure machine (manufactured by Nikon Co.) and then subjected to a post-exposure baking treatment at 100° C. for 90 seconds followed by a development treatment for 65 seconds in a 0.238% by weight aqueous solution of tetramethylammonium hydroxide, rinse in a running stream of water for 30 seconds and drying to complete a patterned resist layer.

The photosensitivity of the photoresist composition in the patterning process described above was estimated by recording the minimum exposure dose in mJ/cm² necessitated for the reproduction of a line-and-space pattern of 0.25 μm line and space widths to give a line-and-space patterned resist layer with a line width to space width ratio of 1:1 as a measure of the photosensitivity to find a value of 25 mJ/cm².

The above obtained line-and-space patterned resist layer of 0.25 μm line width had an orthogonal cross sectional profile standing upright on the substrate surface as examined on a scanning electron microscopic photograph. Further, pattern resolution thereof was complete without patterning failure in a line-and-space patterned resist layer having a line width of as small as 0.20 μm.

In the next place, the resist layer was subjected to a test of dry etching resistance by conducting a dry etching treatment on an etching instrument (Model OAPM-406, manufactured by Tokyo Ohka Kogyo Co.) using a gaseous mixture of oxygen and tetrafluoromethane as the etching gas to find that the rate of film thickness reduction per unit time was 115% based on the rate with a polyhydroxystyrene resin film.

COMPARATIVE EXAMPLE 1

Evaluation tests of a photoresist composition were undertaken in the same manner as in Example 1 except that the photoresist composition was prepared with replacement of the resin prepared in Preparation Example 2 and used in Example 1 with the same amount of the resin prepared in the comparative Preparation Example 3.

The results of the tests were that the photosensitivity of the resist layer was 35 mJ/cm$^2$, the cross sectional profile of the patterned resist layer of 0.25 μm line width was not orthogonal but trapezoidal, patterning in a line-and-space patterned resist layer of 0.20 μm line width was incomplete with patterning failure and the rate of film thickness reduction in the dry etching test was 95% of the rate with a polyhydroxystyrene resin film.

COMPARATIVE EXAMPLE 2

Evaluation tests of a photoresist composition were undertaken in the same manner as in Example 1 except that the photoresist composition was prepared with replacement of the resin prepared in Preparation Example 2 and used in Example 1 with the same amount of the resin prepared in the comparative Preparation Example 4.

The results of the tests were that the photosensitivity of the resist layer was 35 mJ/cm$^2$, the cross sectional profile of the patterned resist layer of 0.25 μm line width was not orthogonal but trapezoidal, patterning in a line-and-space patterned resist layer of 0.20 μm line width was incomplete with patterning failure and the rate of film thickness reduction in the dry etching test was 95% of the rate with a polyhydroxystyrene resin film.

COMPARATIVE EXAMPLE 3

Evaluation tests of a photoresist composition were undertaken in the same manner as in Example 1 except that the photoresist composition was prepared with replacement of the resin prepared in Preparation Example 2 and used in Example 1 with the same amount of the resin prepared in the comparative Preparation Example 5.

The results of the tests were that the photosensitivity of the resist layer was 35 mJ/cm$^2$, the cross sectional profile of the patterned resist layer of 0.25 μm line width was not orthogonal but trapezoidal and the rate of film thickness reduction in the dry etching test was 150% of the rate with a polyhydroxystyrene resin film.

What is claimed is:

1. 2-Hydroxy-3-pinanone acrylate.
2. 2-Hydroxy-3-pinanone methacrylate.

* * * * *